United States Patent
Haase et al.

(10) Patent No.: US 10,694,955 B2
(45) Date of Patent: Jun. 30, 2020

(54) APPARATUS FOR VESSEL CHARACTERIZATION

(71) Applicant: KONINKLIJKE PHILIPS N.V., Eindhoven (NL)

(72) Inventors: Christian Haase, Hamburg (DE); Michael Grass, Buchholz in der Nordheide (DE); Dirk Schaefer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 115 days.

(21) Appl. No.: 16/080,243

(22) PCT Filed: Feb. 28, 2017

(86) PCT No.: PCT/EP2017/054539
§ 371 (c)(1),
(2) Date: Aug. 27, 2018

(87) PCT Pub. No.: WO2017/148877
PCT Pub. Date: Sep. 8, 2017

(65) Prior Publication Data
US 2019/0046047 A1 Feb. 14, 2019

(30) Foreign Application Priority Data

Mar. 4, 2016 (EP) .................................. 16158610

(51) Int. Cl.
*A61B 5/0215* (2006.01)
*A61B 5/107* (2006.01)
(Continued)

(52) U.S. Cl.
CPC ........ *A61B 5/02007* (2013.01); *A61B 5/0035* (2013.01); *A61B 5/0215* (2013.01);
(Continued)

(58) Field of Classification Search
CPC ......... G06T 7/0012; G06T 2207/30101; G06T 2207/30104; A61B 5/02007;
(Continued)

(56) References Cited

U.S. PATENT DOCUMENTS

| 5,009,234 A | 4/1991 | Alt ................................ 128/672 |
| 6,354,999 B1 | 3/2002 | Dgany et al. ................. 600/486 |

(Continued)

FOREIGN PATENT DOCUMENTS

| WO | 200113779 A2 | 3/2001 | ............. A61B 5/00 |
| WO | 2008131303 A2 | 10/2008 | ............. A61B 18/22 |

(Continued)

*Primary Examiner* — Andrew W Johns (57) ABSTRACT

The invention discloses an apparatus (2), a system (1) and a method (100) for characterization of vessels and for vessel modeling. The cross sectional area ($A_1$) of the vessel is derived from pressure measurements ($p_1$, $p_2$) obtained by an instrument (3) from within the vessel. When multiple cross sectional areas ($A_1$, $A_2$) are derived for multiple reference positions ($r_1$, $r_2$) based on pressure measurements ($p_1$, $p_2$, $p_3$) along the vessel, a representation (20, 30) of the vessel can be rendered, without requiring any imaging modality. Furthermore, the effect of the pulsatile blood flow on the elasticity of the vessel walls can be visualized, supporting assessment of a stenosis or an aneurysm formation along the vessel.

10 Claims, 8 Drawing Sheets (51) Int. Cl.
| | |
|---|---|
| *A61B 5/02* | (2006.01) |
| *A61B 5/06* | (2006.01) |
| *A61B 5/00* | (2006.01) |
| *G06T 7/00* | (2017.01) |
| *A61B 6/12* | (2006.01) |
| *A61B 8/08* | (2006.01) |

(52) U.S. Cl.
CPC .......... *A61B 5/02028* (2013.01); *A61B 5/063* (2013.01); *A61B 5/1076* (2013.01); *G06T 7/0012* (2013.01); *A61B 5/02158* (2013.01); *A61B 5/064* (2013.01); *A61B 5/066* (2013.01); *A61B 5/7425* (2013.01); *A61B 6/12* (2013.01); *A61B 8/0841* (2013.01)

(58) Field of Classification Search
CPC .............. A61B 5/02028; A61B 5/0215; A61B 5/02158; A61B 5/1076
See application file for complete search history.

(56) References Cited

U.S. PATENT DOCUMENTS

| | | | |
|---|---|---|---|
| 2004/0254483 A1 | 12/2004 | Zdeblick et al. | ........ A61B 5/02 |
| 2005/0092340 A1 | 5/2005 | Rijskamp | ............... A45D 24/22 |
| 2014/0236492 A1 | 8/2014 | Taylor | .................... A61B 6/504 |
| 2015/0119705 A1 | 4/2015 | Tochterman et al. | ....................... A61B 5/02158 |

FOREIGN PATENT DOCUMENTS

| | | | |
|---|---|---|---|
| WO | 2012123345 A1 | 9/2012 | ............... A61B 8/12 |
| WO | 2016009317 A1 | 1/2016 | ............... A61B 5/00 |

Fig. 13

APPARATUS FOR VESSEL CHARACTERIZATION

CROSS-REFERENCE TO PRIOR APPLICATIONS

This application is the U.S. National Phase application under 35 U.S.C. § 371 of International Application No. PCT/EP2017/054539, filed on Feb. 28, 2017, which claims the benefit of European Patent Application No. 16158610.2, filed on Mar. 4, 2016. These applications are hereby incorporated by reference herein.

FIELD OF THE INVENTION

The invention relates to an apparatus, system and method for characterization of vessels and for vessel modeling.

BACKGROUND OF THE INVENTION

A typical technique for identifying stenotic regions in a blood vessel is using angiography, whereas the functional impact of the stenosis is quantified with the fractional flow reserve (FFR) technique. FFR is calculated from the ratio of pressures at the distal and proximal ends of the stenosis, measured with a sensor positioned at the tip of a wire. The FFR value is a measure of the severity of the stenosis, and it can be established whether the stenosis limits blood flow within the vessel to an extent that treatment is required. Common treatment options include angioplasty, stenting or bypass.

Angiography, a fluoroscopy imaging technique in conjunction with radio-opaque contrast agents, can be used to visualize the vasculature of a patient. Due to the nature of the technique, only the flow of the contrast agent can be imaged with fluoroscopy, therefore the cross-sectional shape of the lumen remains unknown, since the vessel wall and the surrounding tissue are not imaged. The weakness of the technique is that the cross-sectional shape of the stenosis can only be roughly estimated even by using multiple projections. Furthermore, such a visual evaluation of the stenotic region may be obstructed by other vessels that overlap the stenosis in the image, as well as by image artefacts and noise.

US 2015/0119705 A1 describes a method for evaluating a vessel of a patient based on obtaining physiology measurements from a first instrument and a second instrument positioned within the vessel of the patient while the second instrument is moved longitudinally through the vessel from a first position to a second position and the first instrument remains stationary within the vessel. The physiological measurements are based on local blood pressure measurements and the derived values such as FFR are presented on an angiographic image of the vessel. The output image is a visualization of vessels colorized according to the changes in pressure along the vessels, or a visualization of vessels by using a heat map representing FFR values.

SUMMARY OF THE INVENTION

It is an object of the invention to provide an apparatus for simplifying the characterization of the vessel. According to the invention, this object is realized by an apparatus for characterizing a vessel of a living being, the apparatus configured to:

receive from an instrument within the vessel a first pressure measurement signal at a first measurement location and a second pressure measurement signal at a second measurement location;

derive a first cross sectional area for a first reference position of the vessel based on the first and second pressure measurement signals.

The apparatus is configured to derive the cross sectional area of the vessel based on two pressure measurements at two distinct locations within the vessel, without needing to use information from imaging techniques such as fluoroscopy in conjunction with radio-opaque contrast agents.

In an embodiment, the apparatus is further configured to receive from the instrument within the vessel a third pressure measurement signal at a third measurement location and to derive a second cross sectional area for a second reference position of the vessel based on the third pressure measurement signal and one of the first and second pressure measurement signals. The benefit of deriving multiple cross sectional areas at multiple reference positions along the vessel is that the condition of the vessel can be evaluated based on the change of the cross sectional diameters at the respective reference positions. In such a way detection of potential narrowing or widening of the vessel is possible without using imaging techniques.

In an embodiment, the apparatus is further configured to render a representation of the vessel based on the first and second cross sectional areas and the first and second reference positions. A graphical representation based on the distance between the two reference positions and the cross sectional areas at the respective locations improves the characterization of the vessel by allowing a quick visual interpretation of the condition of the vessel.

In a further embodiment, the first, second and third pressure measurement signals are temporal measurement signals of a pulsatile blood flow within the vessel; the first and second cross sectional areas are derived for subsequent phases of the pulsatile blood flow; and the representation of the vessel comprises a sequence of representations of the vessel corresponding to the subsequent phases of the pulsatile blood flow. The pulsatile blood flow is caused by the cardiac heart beat cycle. The graphical representation of the vessel depending on the phases of the pulsatile blood flow allows an improved evaluation of potential conditions of the vessel where elasticity of the vessel segments are influenced by the magnitude of the blood pressure. Such conditions may be an asymmetric narrowing of the vessel, formation of aneurysm, etc.

In an embodiment, the apparatus is further configured: to receive morphological information of the vessel from an imaging unit; to render a composite representation comprising: a morphological representation of the vessel based on the morphological information and the representation of the vessel based on the first and second cross sectional areas and the first and second reference positions. The representation based on morphological information received from the imaging unit enriches the information available for evaluation of the condition of the vessel, providing the physician with additional information on the orientation of the vessels within the body of the patient.

In a further embodiment, the apparatus is configured to ascertain the first measurement location and the second measurement location based on information provided by a tracking unit on the position of at least a marker component of the instrument. Tracking the position of components of the instrument may be achieved by various techniques ranging from electromagnetic tracking to optical shape sensing.

In another aspect of the invention a system for characterizing a vessel of the living being is presented, the system comprising the apparatus according to the invention and the instrument configured for providing the first pressure measurement signal at the first measurement location and the second pressure measurement signal at the second measurement location within the vessel. In an embodiment, the instrument is configured to provide a third pressure measurement signal at a third measurement location. In an embodiment the instrument comprises a first, a second and a third pressure sensor for providing the first, second and third pressure measurement signals at the first, second and third measurement locations, respectively. In an alternative embodiment, the instrument comprises a single pressure measurement sensor, and the instrument is configured to provide the first, second and third pressure measurement signals by subsequent changes of a position of the pressure sensor along the vessel. The subsequent changes of position of the pressure sensor within the vessel may occur by advancing or retrieving (pullback) the instrument within the vessel, or a part of the instrument comprising the pressure sensor. The advantage of a single pressure sensor integrated into the instrument is a simpler construction, while the advantage of integrating multiple sensors into the instrument is that during the process of characterization of the vessel there is no need for changing position of the instrument.

In an embodiment, the system is further configured to receive morphological information of the vessel from an imaging unit; to render a composite representation comprising: a morphological representation of the vessel based on the morphological information and the representation of the vessel based on the first and second cross sectional areas and the first and second reference positions. A combination of the representation of the vessel based on pressure measurements and the representation based on morphological information enriches the possibilities for evaluation of the vessel condition. An overlay of the two representations may be based on visual interpretation by the physician of particular features (narrowing, widening, bends, etc.) of the vessel from the two representations, and it may be enabled for the physician by a drag and drop technique applied for one of the representations. Alternatively, the overlay may be based on automatic registration by a computer vision algorithm. Once the two representations are registered the measurement locations are also known within the morphological representation. This would replace the need for device tracking, while the intravascular pressure data can be displayed at the correct location within the morphological representation.

In a further embodiment, the system comprises the imaging unit, wherein the system is further configured to ascertain the first measurement location and the second measurement location based on detection of at least a marker component of the instrument by the imaging unit; and to register the first and second measurement locations with the morphological representation of the vessel. The imaging unit may be a radiological imaging unit, a magnetic resonance imaging unit or ultrasound imaging unit. The detection of the instrument or a part of the instrument may be enabled by specific markers integrated into the instrument or by using combination of various materials in the composition of the instrument, which are differentiable by the respective imaging modalities. Once the measurement locations are registered with the morphological representation, the representation of the vessel based on pressure measurements can take into account the bends of the vessel.

In yet another aspect of the invention a method of characterizing a vessel of a living being is presented, the method comprising:

receiving from an instrument within the vessel a first pressure measurement signal at a first measurement location and a second pressure measurement signal at a second measurement location; and deriving a first cross sectional area for a first reference position of the vessel based on the first and second pressure measurement signals.

The cross sectional area of the vessel can be derived based on two pressure measurements at two distinct locations within the vessel, which simplifies the procedure since for the determination of the cross sectional area of the vessel a radiological imaging unit, such as used for fluoroscopy imaging in conjunction with radio-opaque contrast agents, is not necessary.

In a further embodiment, the method comprises:

receiving from the instrument within the vessel a third pressure measurement signal at a third measurement location;

deriving a second cross sectional area for a second reference position of the vessel based on the third pressure measurement signal and one of the first and second pressure measurement signals;

rendering a representation of the vessel based on the first and second cross sectional areas and the first and second reference positions.

By deriving multiple cross sectional areas at multiple reference positions along the vessel the condition of the vessel can be evaluated based on the change of the cross sectional areas at the respective reference positions. A representation of the vessel with the cross sectional areas at the respective reference positions is an important visual support for the physician when assessing presence of stenosis and/or aneurysm along the vessel.

Additional aspects and advantages of the invention will become more apparent from the following detailed description, which may be best understood with reference to and in conjunction with the accompanying drawings.

DETAILED DESCRIPTION OF EMBODIMENTS

Figure 1:
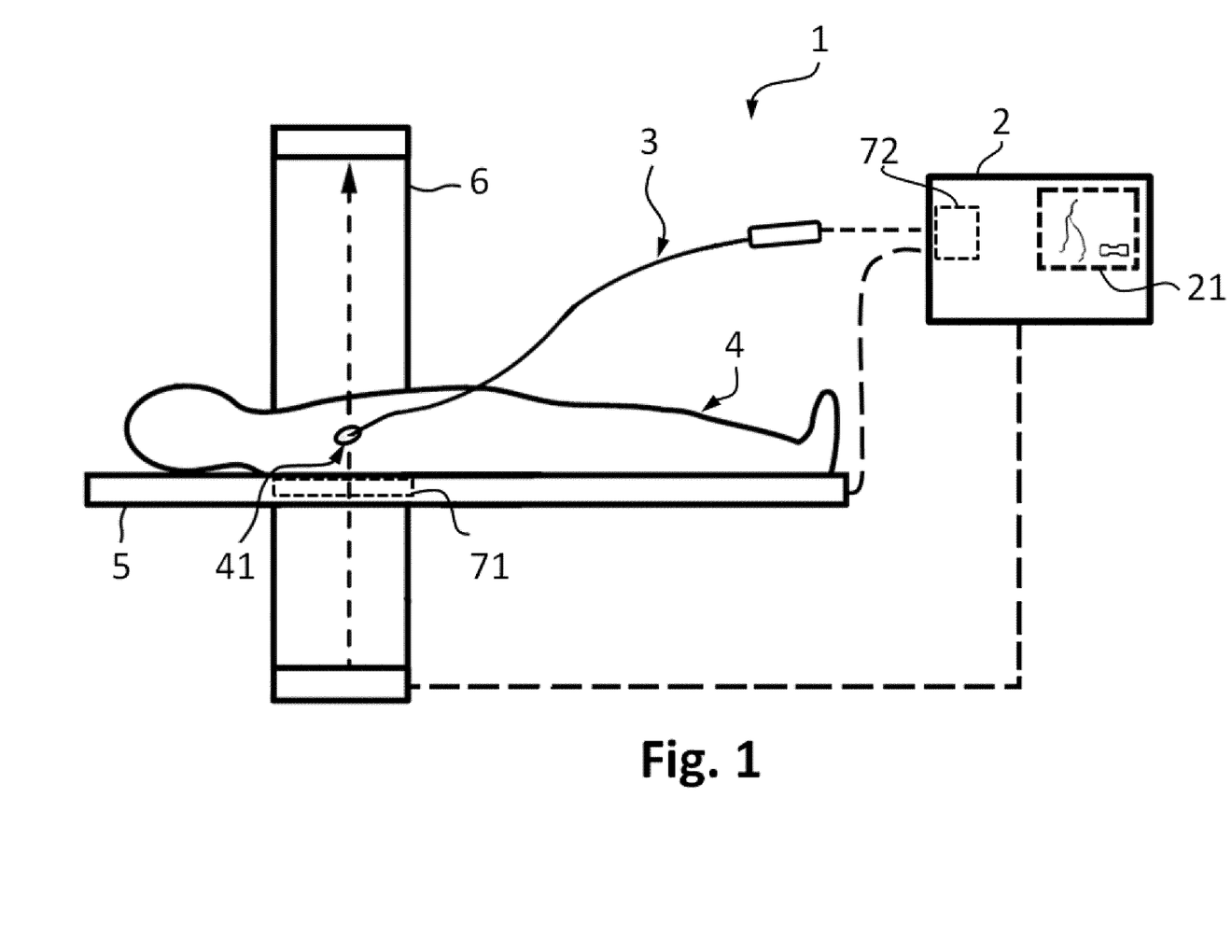
FIG. 1 shows schematically and exemplarily an embodiment of the system for characterizing a vessel of a living being, according to the invention.

In FIG. 1 an embodiment of the system 1 for characterization of a vessel of a living being 4 is presented, wherein the living being may be a person or an animal. The system 1 comprises an apparatus 2 and an instrument 3, wherein the instrument is configured to provide pressure measurement signals from within a vessel of a portion 41 of the circulatory system of the patient 4, and the apparatus 2 is configured to ascertain characteristics of the vessel based on the pressure measurements. The apparatus 2 comprises a display 21 for rendering the characteristics of the vessel. Alternatively, the apparatus may be configured to provide signals to an external display on which the designated characteristics are presented to the physicians.

In an embodiment, the system comprises an imaging unit 6 for acquiring two-dimensional or three-dimensional morphological information of the vessel structure of interest upon injection of a contrast agent bolus into the targeted vasculature. The injection of the contrast agent bolus into the targeted vasculature is performed either with the instrument 3 or with a different medical instrument. Two-dimensional or three-dimensional morphology of the vasculature can be obtained by various well established techniques such as: radiological angiography including computed tomography angiography (RA), magnetic resonance angiography (MRA) or ultrasound imaging (UI). For the respective imaging modalities contrast agents are available, for instance radiological contrast agent for RA, a gadolinium-based substance for MRA, echogenic contrast agent comprising microbubbles for extracorporal or intracorporal UI.

Figure 2:
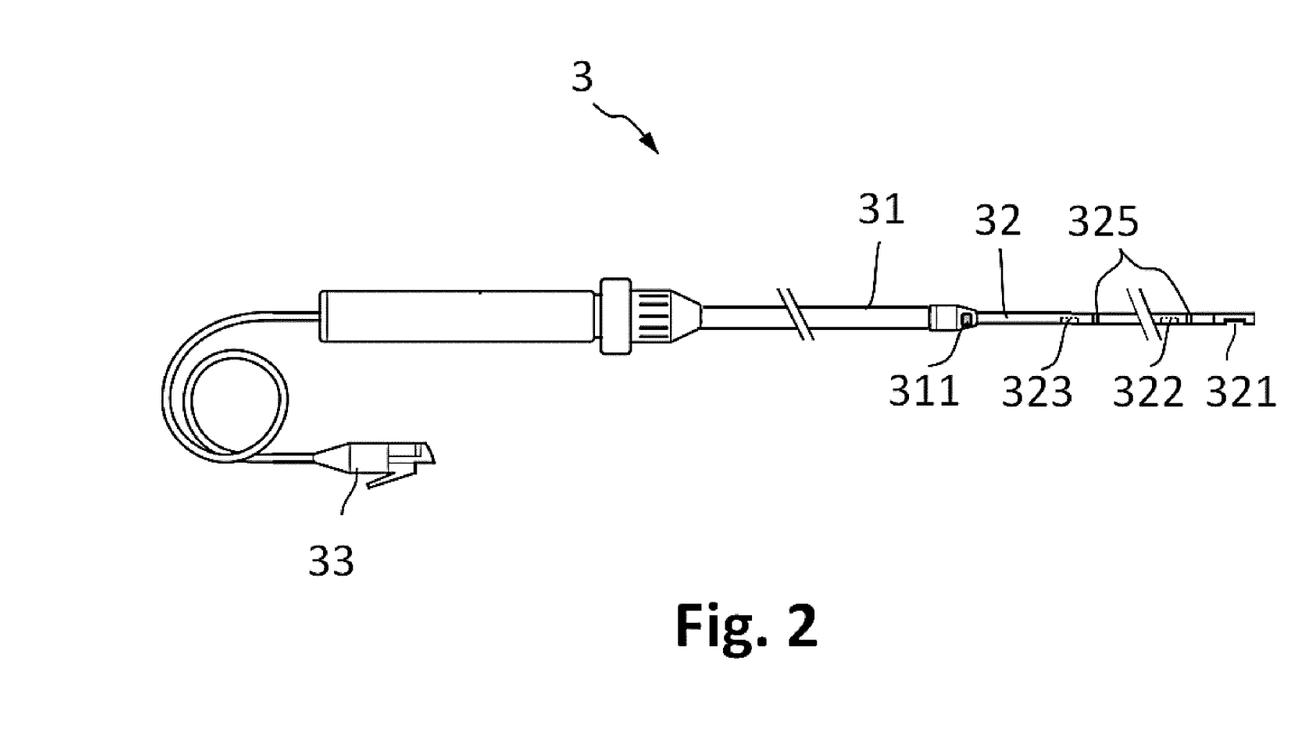
FIG. 2 shows schematically and exemplarily an embodiment of the instrument used for pressure measurement within the vessel.

An exemplarily embodiment of the medical instrument 3 used for pressure measurement within the vessel is a guiding catheter-guidewire assembly, shown in FIG. 2. The guiding catheter 31 is formed by a hollow handgrip and an elongated flexible tubular shaft comprising an inner lumen, and it is configured to movably receive the guidewire 32 formed by a flexible shaft. A pressure sensor 311 is integrated into the distal portion of the guiding catheter 31 for measurement of a blood pressure. The guidewire 32 also comprises at least a pressure sensor 321 integrated into its distal portion, for measurement of blood pressure at multiple locations along the blood vessel by using a pullback motion of the guidewire with respect to the blood vessel. Typical example for such guidewire is the Verrata® pressurewire, manufactured by Volcano Corporation.

In an embodiment, the guidewire 32 may comprise multiple sensors 321,322,323, distributed spatially along its distal portion, such that multiple pressure measurements along the vessel can be acquired in a stationary position of the guidewire with respect to the blood vessel, without the classical guidewire pullback being required.

In an alternative embodiment, the instrument 3 may be formed as a catheter comprising a handgrip, an elongated flexible tubular shaft with an inner lumen configured to movably receive a telescopically extensible flexible shaft reaching distal to the tubular elongated shaft. The connection of the instrument 3 to the apparatus 2 is realized either by a connector 33 or a wireless connection. A pressure sensor 311 is integrated into the distal portion of the elongated tubular shaft, while at least one pressure sensor 321 is integrated into the distal portion of the telescopically extendable part of the medical instrument.

In yet another embodiment the instrument 3 may comprise only the guidewire 32 with at least one integrated pressure sensor 321 into its distal region.

The pressure sensors may employ one of the various techniques for blood pressure measurements, for instance the change of piezoresistive property upon pressure, fluidic transduction of a deflection of a diaphragm to a mechanical or an electrical signal, and capacitive readout of a suspended membrane over a substrate.

Figure 3:
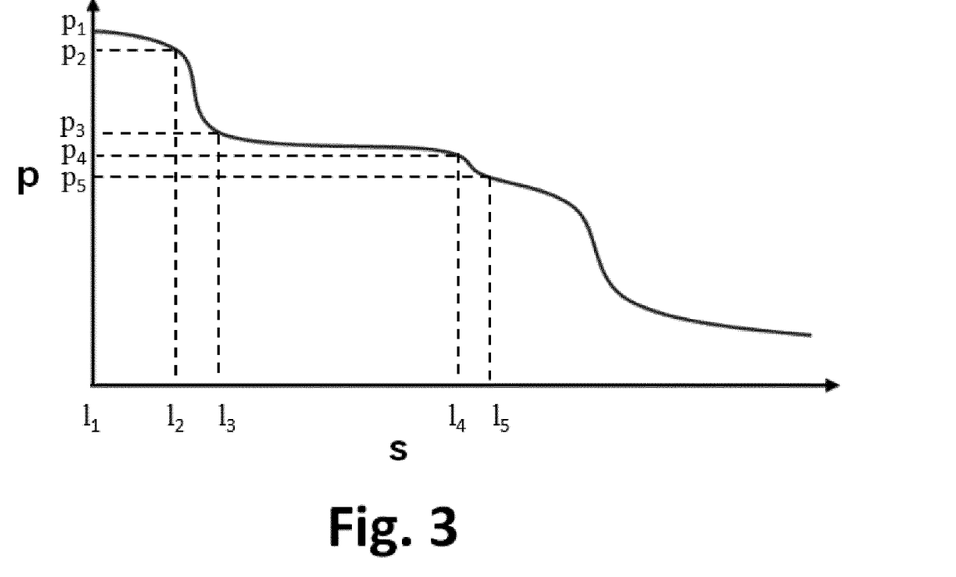
FIG. 3 shows exemplarily a representation of the pressure measurements along a vessel segment.

FIG. 3 shows exemplarily a representation of the pressure measurement p along a vessel segment s. The instrument within the vessel provides a first pressure measurement signal $p_1$ at a first measurement location $l_1$ in the vessel and a second pressure measurement signal $p_2$ at a second measurement location $l_2$. The pressure drop for the segment $s_1$ defined by the two measurement locations is $\Delta p(s_1) = p_2 - p_1$. Using a linear order approximation the volumetric flow Q along a tubular structure is $Q = \Delta p / R$, where R is the resistance of the vessel to flow. Higher order terms to relate $\Delta p$ and Q could be used as well. The resistance R is a function of the cross sectional area A of the vessel lumen. This relation can be determined by a numerical fluid dynamics model, e.g. in a simple model based on the Hagen-Poiseuille equation the resistance $R = 8 \mu s_1 / \pi r^4$, where $s_1$ is the distance between measurement locations $l_1$ and $l_2$, r is the radius of the vessel lumen, and $\mu$ is the dynamic viscosity of blood. Alternatively, a more complex fluid dynamics model may be used.

The corresponding inverse function can then be used to calculate the cross sectional area of the vessel lumen from a known resistance. By using a constant volumetric blood flow value and the pressure drop $\Delta p(s)$ for various segments of the vessel defined by multiple pressure measurement locations, the cross sectional area A(s) can be calculated at any position along the vessel segment with the relationship:

$$A(s) = A(R(s)), \text{ where } R(s) = \Delta p(s)/Q.$$

The flow rate can be obtained by an additional intravascular measurement, or derived in any other suitable way. A volumetric flow rate as well as other related quantities e.g. flow velocity or average peak flow velocity can be used.

If the relation A(R(s)) is a homomorphism, the relative variation $A(R(s_1))/A(R(s_2))$ can be calculated without needing the flow rate as input.

Figure 4:
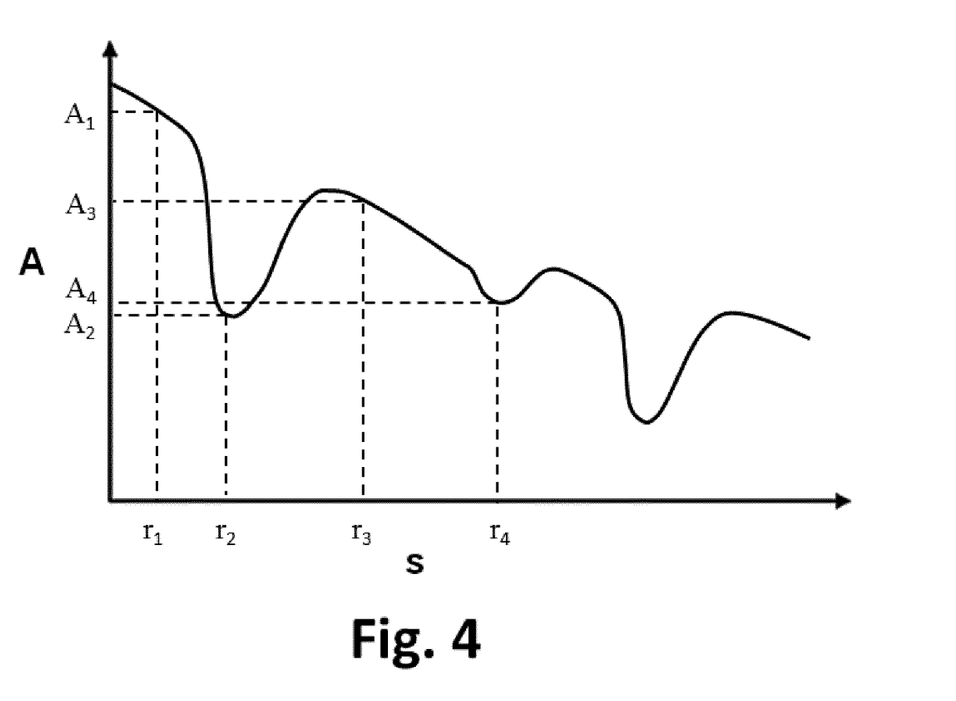
FIG. 4 shows exemplarily a representation of the cross sectional areas of the vessel ascertained based on the pressure measurements along the vessel segment.
Figure 5:
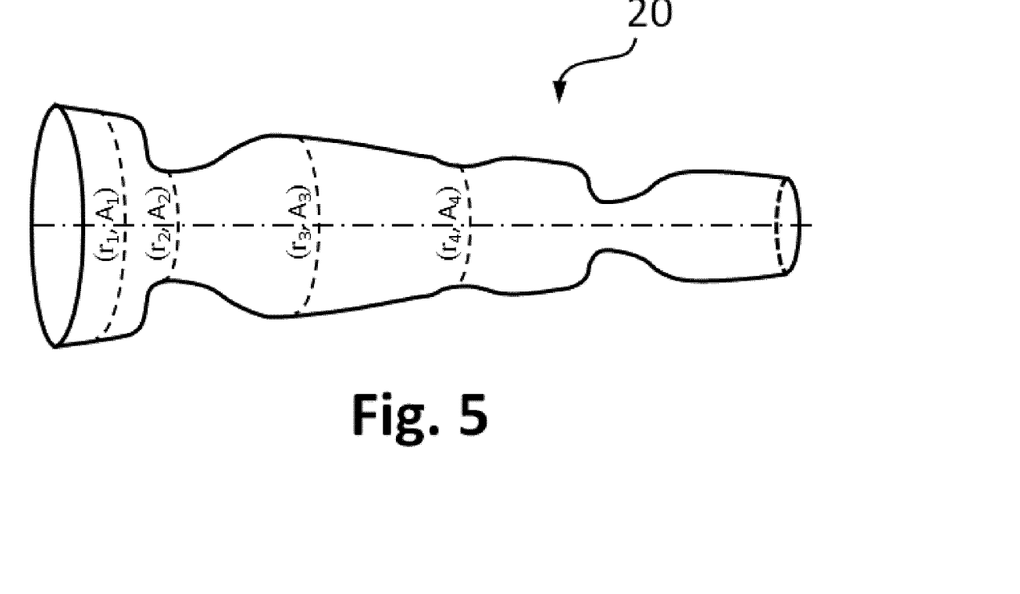
FIG. 5 shows a three-dimensional representation of the vessel model based on the cross sectional areas along the vessel segment.
Figure 6:
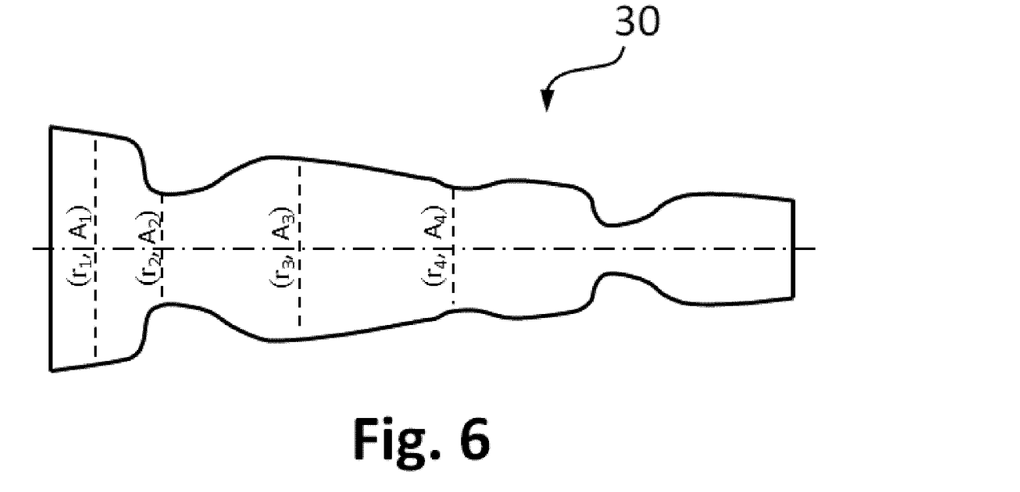
FIG. 6 shows a two-dimensional projection of the three-dimensional vessel model.

The measurement locations chosen in FIG. 3 are distant, in order to support the exemplary elucidation of the invention, however the measurement locations can be very close to each other, which can be achieved either by taking pressure measurements with the pressure wire having a slow pullback, or by making small incremental steps during the pullback motion. The cross sectional area $A_1$ is derived for the segment $s_1$ defined by the pressure measurement locations $l_1$ and $l_2$. When multiple pressure measurements $p_1$ to $p_5$ are provided at multiple measurement locations $l_1$ to $l_5$, like for example in FIG. 3, then the reference positions $r_1$ to $r_4$ can be defined along the respective vessel segments $s_1$ to $s_4$, and the cross sectional areas $A_1$ to $A_4$ can be assigned to the respective reference positions. The points $(r_1, A_1)$ to $(r_4, A_4)$ can be connected by using an appropriate interpolation function for providing a smooth transition of the cross sectional areas between the reference positions, resulting in a representation illustrated in FIG. 4. The reference positions are located along the respective vessel segments, and they may be chosen as the middle of the segments, one of the measurement locations defining the respective segments, or they may be determined by using a function depending on the derived cross sectional area for the respective segment and that of the adjacent segment, for instance by using a weighted average. An intuitive illustration of the cross sectional areas in function of the respective reference positions along the blood vessel is a three-dimensional graphical representation 20 shown in figure FIG. 5. In an embodiment shown in FIG. 6, a two-dimensional projection 30 of the three-dimensional vessel model 20 is presented to the physician on the display 21. A further alternative representation may comprise the diameters at the respective reference positions, which can be derived from the respective cross sectional areas. The cross sectional areas and/or diameters can be derived for the entire length of the blood vessel defined by the locations of the first and last pressure measurements, based on the interpolation function.

In a further embodiment, the instrument is configured to provide blood flow measurement besides the pressure measurements, hence the volumetric blood flow is calculated based on the blood flow measurement, which is then used in the calculation of the cross sectional areas A(s) and the diameters along the vessel.

The system 1 in FIG. 1 may further comprise a tracking unit 72 for receiving temporal information about the location of the instrument 3 within the vasculature of the person 4. Spatial position tracking of the instrument may be based on one of an electromagnetic, an optical, an ultrasound, an electrical impedance and a radiological principle. Electromagnetic tracking of instruments is based on detection of an external electromagnetic field by electromagnetic sensors integrated into the instrument. The electromagnetic sensors, functioning as markers 325 in the electromagnetic field, are integrated into the distal portion of the instrument 3, for instance in the guiding catheter 31 and the guidewire 32, located at predetermined relative positions with respect to the pressure sensors 311 and 321, as shown in FIG. 2. The electromagnetic field generator 71 may be removably attached to either the support means 5 of the person 4 or to the imaging unit 6. Multiple electromagnetic sensors integrated into the instrument 3 allow simultaneous localization of multiple points along the instrument 3, based on which the shape of a segment of the instrument 3 can be reconstructed by connecting the localized points.

In an alternative embodiment, the tracking of the temporal location of the instrument is derived from laser radiation. For optical tracking, the instrument comprises multiple optical fibers or a multi-core optical fiber extending from distal end to a proximal portion of the instrument 3, typically the handgrip, where optical connection to the tracking unit 72 is facilitated. The tracking unit 72 comprises a laser radiation generator configured to transmit laser radiation into at least an optical fiber integrated within the instrument, and an optical detector configured to receive reflections from within the at least one optical fiber. The shape of the at least one optical fiber, hence that of the instrument 3 is derived by processing optical reflection signals from within the optical fibers, received by a detector. The reflections of the laser radiation from within the at least one optical fiber are indicative of local strains to which the instrument 3 is exposed in tortuous vessel branches. Shape determination of a medical instrument based on optical shape sensing is described in details in WO 2008131303 A2. Optical shape sensing makes possible the localization of any points along the at least one optical fiber integrated into the instrument 3 for all instances.

In an alternative embodiment the location tracking technique of the instrument is based on electrical impedance measurement. Electrical signals are sent into the patient by multiple electrically conductive patches distributed onto the body of the person 4. The distal portion of the trackable instrument 3 comprises spatially distributed electrically conductive electrodes, functioning as markers 325 for their relative positions with respect to the electrically conductive patches. The electrical impedances derived from the received electrical signals are indicative of the locations of the conductive electrodes in the region of interest comprising the target vasculature.

In yet a further embodiment the location of the instrument 3 is tracked by using the imaging unit. The instrument 3 comprises specific markers 325 visible with the imaging modality used in the procedure. In case of radiological imaging, the instrument 3 comprises radiological markers along the distal portion of the instrument 3 at predetermined locations with respect to the pressure sensors 311 and 321, whereas for ultrasound imaging the instrument 3 comprises ultrasound sensors as markers 325, distributed spatially along the instrument. Upon excitation of the external ultrasound imaging unit with an electric signal, the generated ultrasound signal is transmitted into the body of the person 4 and a portion of the ultrasound signal is received by the ultrasound sensors integrated into the instrument 3. The time of flight of the ultrasound signals is indicative of the positions of the ultrasound sensors integrated into the instrument 3 with respect to the external ultrasound imaging unit, and by processing the signals the shape of the distal portion of the instrument comprising the ultrasound sensors can be reconstructed.

Figure 7:
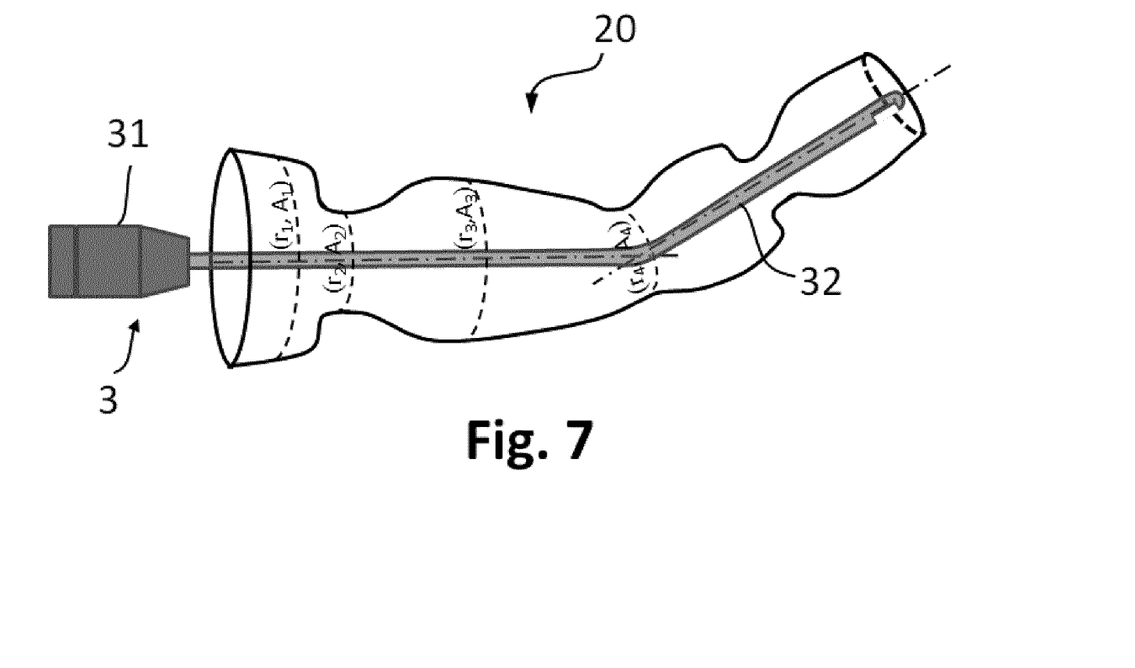
FIG. 7 shows a three-dimensional representation of the vessel model by taking into account the shape of the position tracked instrument.
Figure 8:
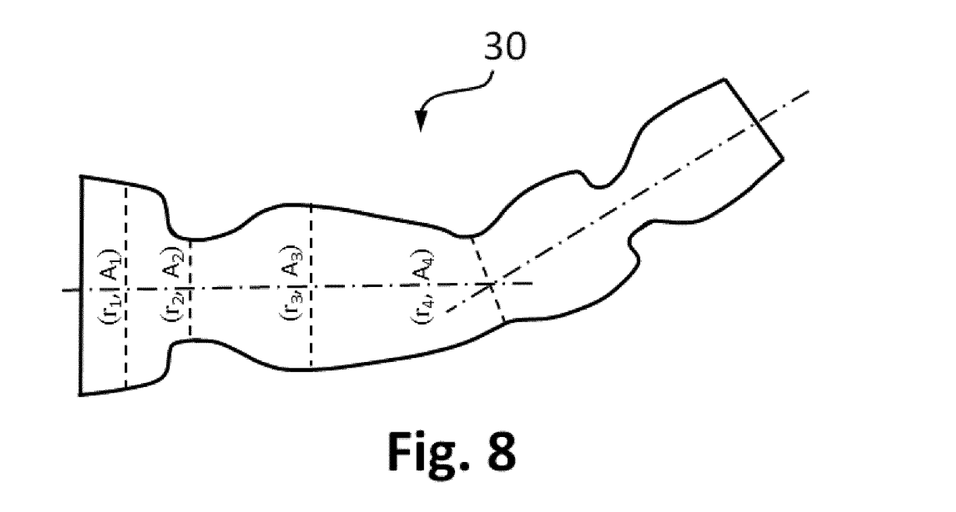
FIG. 8 shows the two-dimensional projection of the three-dimensional vessel model by taking into account the shape of the position tracked instrument.

With the reconstruction of the shape of the instrument 3 based on the tracked locations of markers 325 spatially distributed along the distal portion, the three-dimensional graphical representation 20 of the blood vessel can be improved by accounting for the bends encountered by the instrument along the vessel segment of interest, as illustrated in FIG. 7. The bends of the vessel segment may also be represented in the two-dimensional projection 30, as shown in FIG. 8.

Figure 9:
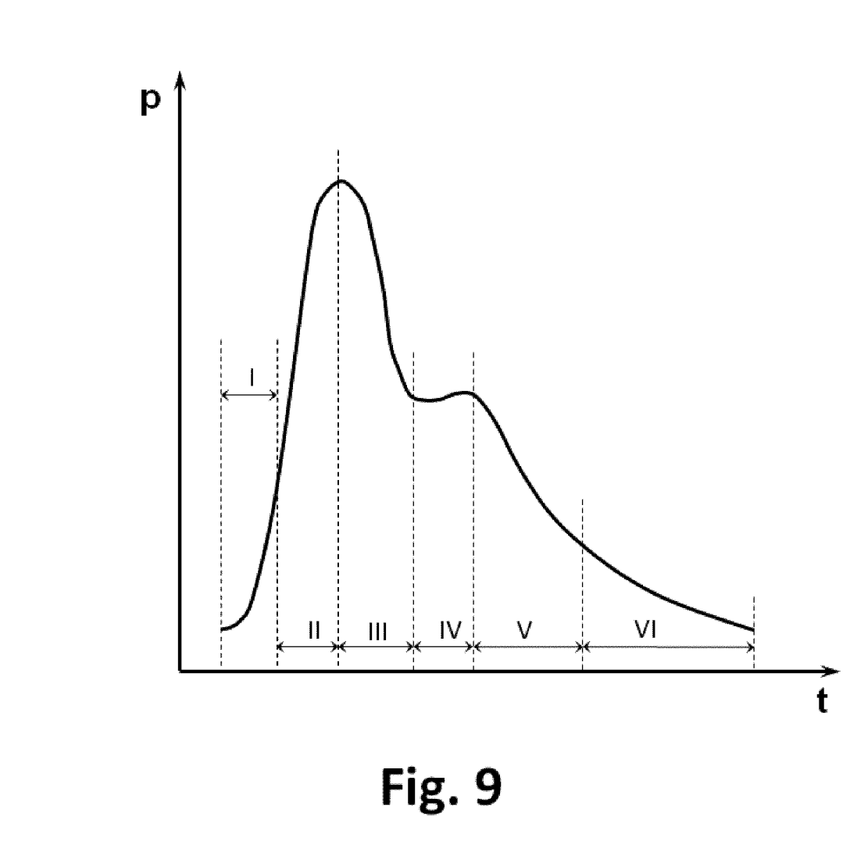
FIG. 9 shows exemplarily a pulsatile blood pressure measurement.

The blood flow in the vessel has a pulsatile nature, illustrated in FIG. 9, and the cross sectional area of the vessel can be derived based on the pressure measurement signals averaged over a single cardiac cycle or over multiple cardiac cycles for the respective measurement locations. In an alternative embodiment, the cross sectional areas of the vessel are derived for subsequent phases I to VI of the pulsatile blood flow, and the representation of the vessel comprises a sequence of representations of the vessel corresponding to the subsequent phases of the pulsatile blood flow. The vessel may be displayed to the physician as a succession of frames of graphical representations rendered for the consecutive phases I to VI, or alternatively the physician may select particular phases of interest of the cardiac cycle for evaluation of potential conditions of the vessel where elasticity of the vessel segments may play a role, for instance in the evaluation of an asymmetric narrowing of the vessel and presence of an aneurysm.

Figure 10:
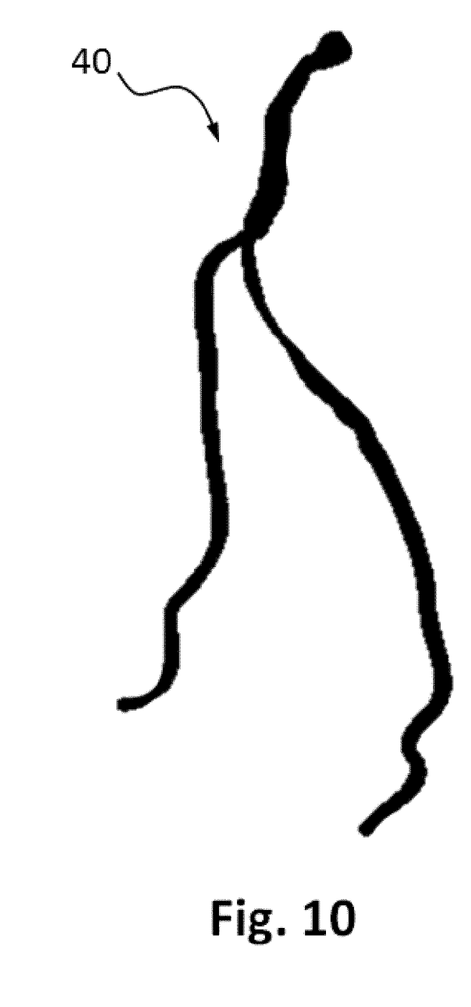
FIG. 10 shows schematically and exemplarily the morphology of a branching vessel obtained by angiography.
Figure 11:
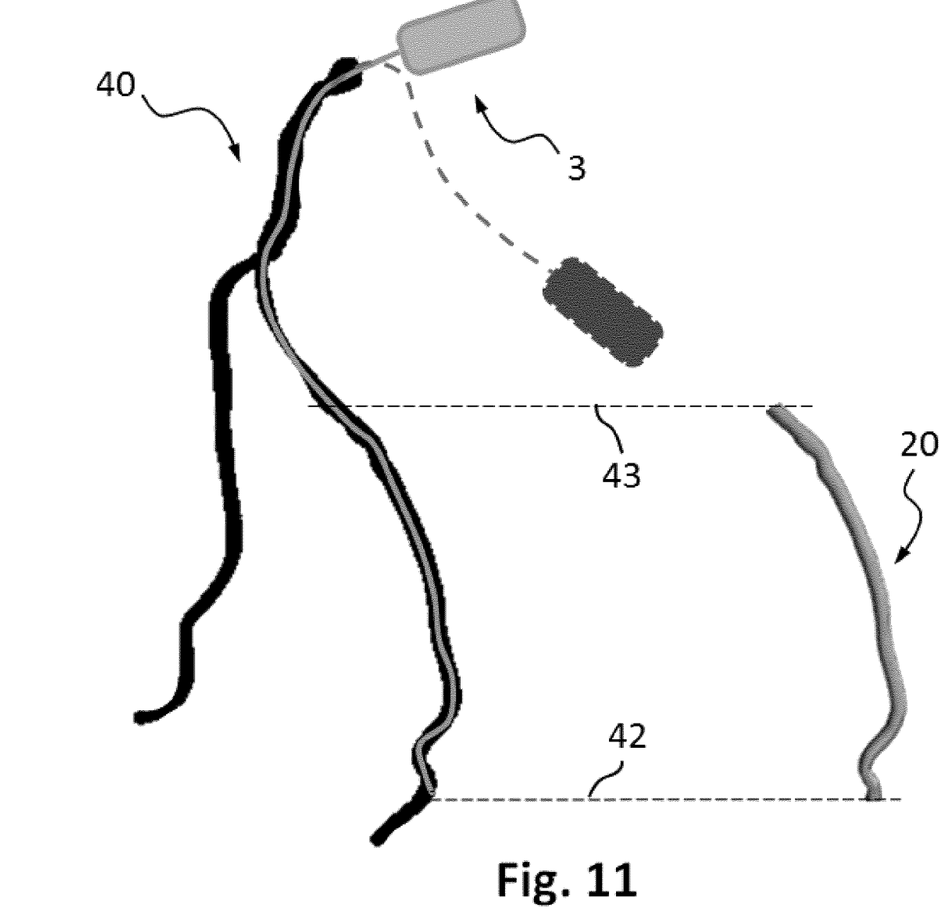
FIG. 11 shows schematically and exemplarily a three-dimensional vessel model generated by using pressure measurements during pull-back of the instrument.

In an embodiment, the imaging unit 6 provides two-dimensional or three-dimensional morphological information of the vessel structure of interest upon injection of a contrast agent bolus in the targeted vasculature, and the morphology 40 of the vessel is rendered on the display 21, as shown in FIG. 10. The shape of the instrument may be reconstructed and visualized as an overlay of the instrument 3 on the vessel morphology 40. In FIG. 11 the instrument 3 is pulled back from a position 42 of its distal end to a position 43, while pressure measurement signals are acquired along the pullback length with the pressure sensor integrated into the distal region of the instrument. The position of the distal tip is continuously visualized by the imaging unit, therefore the trajectory of the tip can be reconstructed.

Figure 12:
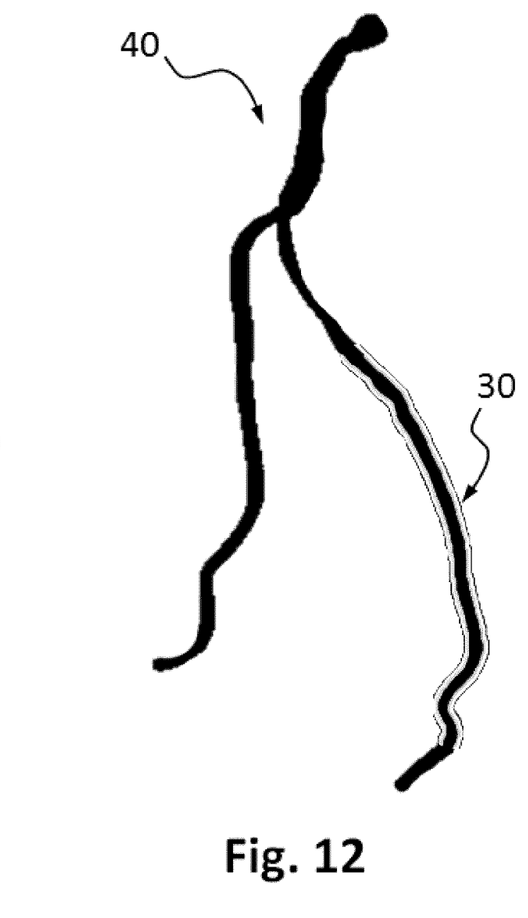
FIG. 12 shows schematically and exemplarily a two-dimensional projection of the vessel model superimposed onto the morphological representation of the branching vessel.

The three-dimensional graphical representation 20 of the vessel model can be obtained by combination of the reconstructed trajectory of the distal tip of the instrument and the derived cross sectional areas of the vessel based on the pressure measurements along the pullback distance. The vessel model is presented separate from the vessel morphology to the physician, and the physician may use a user interface such as a touch screen or pointer means to superimpose the three-dimensional vessel model 20 onto the vessel morphology 40. A further alternative is the registration of the location information of the distal end or a portion of the distal region of the instrument comprising markers 325 during the pullback motion to the two-dimensional angiographic projection or to the three-dimensional angiographic representation. The two-dimensional projection 30 or the three-dimensional representation 20 of the vessel model can be gradually superimposed onto the vessel morphology 40 as the pressure measurements are processed and the cross sectional areas of the vessel are derived for the respective positions of the distal tip of the instrument, as shown in FIG. 12. With shape reconstruction of the instrument 3 based on optical shape sensing and by using multiple pressure sensors spatially distributed along the distal portion of the instrument, the two-dimensional projection 30 or the three-dimensional representation 20 of the vessel can be superimposed onto the vessel morphology 40 while the instrument is stationary with respect to the vessel, hence without requiring a pullback of the instrument.

Figure 13:
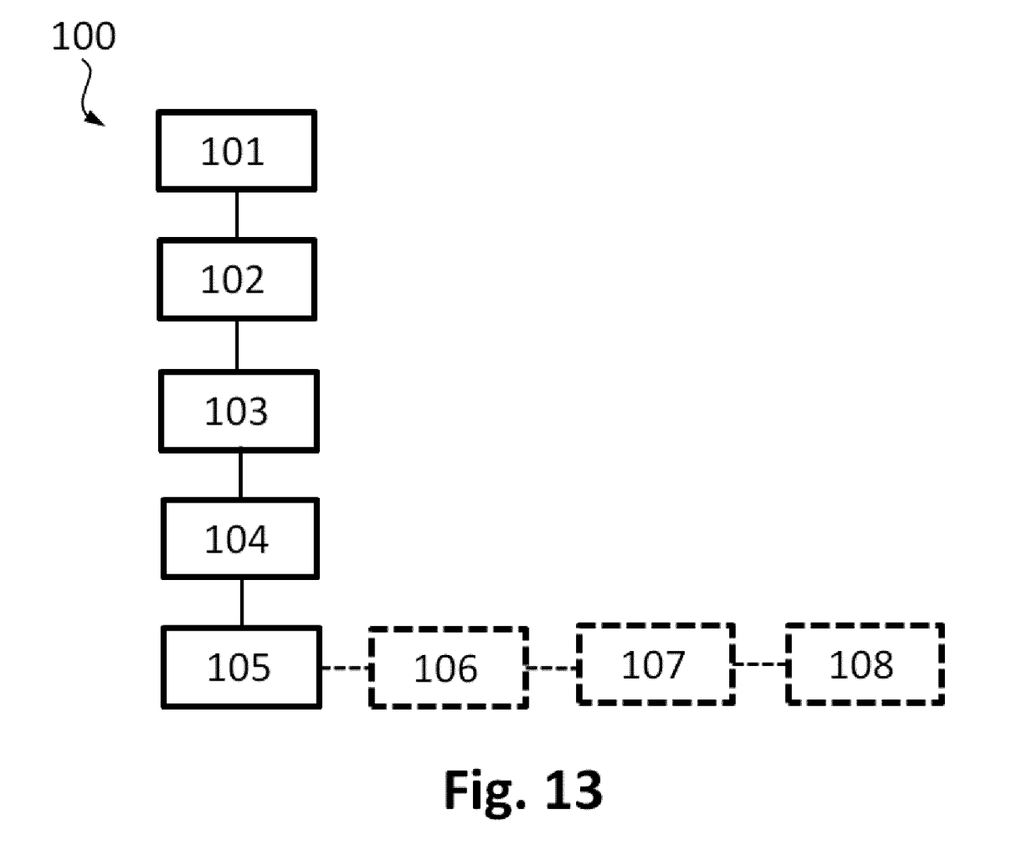
FIG. 13 shows schematically a method of characterizing a vessel of a living being.

In FIG. 13 a method 100 of characterizing a vessel of a living being is presented, comprising: receiving 101 from an instrument 3 within the vessel a first pressure measurement signal $p_1$ at a first measurement location $l_1$ and a second pressure measurement signal $p_2$ at a second measurement location $l_2$; and deriving 102 a first cross sectional area $A_1$ for a first reference position $r_1$ of the vessel based on the first and second pressure measurement signals $p_1,p_2$. In an embodiment the method further comprises: receiving 103 from the instrument within the vessel a third pressure measurement signal $p_3$ at a third measurement location $l_3$; deriving 104 a second cross sectional area $A_2$ for a second reference position $r_2$ of the vessel based on the third pressure measurement signal $p_3$ and one of the first and second pressure measurement signals $p_1,p_2$; and rendering 105 a representation of the vessel based on the first and second cross sectional areas $A_1,A_2$ and the first and second reference positions $r_1,r_2$.

In an embodiment the method may further comprise: receiving 106 morphological information of the vessel from an imaging unit 6; rendering 107 a morphological representation 40 of the vessel based on the morphological information; and composing 108 the morphological representation 40 of the vessel with either the three-dimensional vessel model 20 or the two-dimensional projection 30 of the vessel model rendered based on the first and second cross sectional areas $A_1,A_2$, and the first and second reference positions $r_1,r_2$.

Although the cross sectional area of the vessel is derived from the pressure measurement signals in the exemplary description, it can be understood and effected by those skilled in the art in practicing the claimed invention that a diameter, a radius or a perimeter can be derived from the cross sectional area of the vessel by simple mathematical formulas, therefore the cross sectional area of the vessel in the claimed invention should not be construed as limiting the scope of the invention.

A single unit or device may fulfill the functions of several items recited in the claims. The mere fact that certain measures are recited in mutually different dependent claims does not indicate that a combination of these measures cannot be used to advantage.

In the claims, the word "comprising" does not exclude other elements or steps, and the indefinite article "a" or "an" does not exclude a plurality.

Any reference signs in the claims should not be construed as limiting the scope.

The invention claimed is:

1. An apparatus for characterizing a vessel of a living being, the apparatus comprising a processor configured to:
    receive from an instrument within the vessel a first temporal pressure measurement signal ($p_1$) at a first measurement location ($l_1$), a second temporal pressure measurement signal ($p_2$) at a second measurement location ($l_2$) and a third temporal pressure measurement signal ($p_3$) at a third measurement location ($l_3$) of a pulsatile blood flow within the vessel;
    derive a first cross sectional area ($A_1$) for a first reference position ($r_1$) of the vessel based on the first and second pressure measurement signals ($p_1,p_2$);
    derive a second cross sectional area ($A_2$) for a second reference position ($r_2$) of the vessel based on the third pressure measurement signal ($p_3$) and one of the first and second pressure measurement signals ($p_1,p_2$), the first and second cross sectional areas ($A_1,A_2$) derived for subsequent phases (I-VI) of the pulsatile blood flow;
    render a representation of the vessel based on the first and second cross sectional areas ($A_1,A_2$) and the first and second reference positions ($r_1,r_2$), the representation of the vessel comprising a sequence of representations of the vessel corresponding to the subsequent phases (I-VI) of the pulsatile blood flow.

2. The apparatus according to claim 1, wherein the processor is further configured to:
    receive morphological information of the vessel from an imaging unit;
    render a composite representation comprising:
        a morphological representation of the vessel based on the morphological information; and
        the representation of the vessel based on the first and second cross sectional areas ($A_1, A_2$) and the first and second reference positions ($r_1, r_2$).

3. The apparatus according to claim 1, wherein the processor is further configured to ascertain the first, second and third measurement locations ($l_1, l_2, l_3$) based on information provided by a tracking unit on the position of at least a marker component of the instrument.

4. A system for characterizing a vessel of a living being, comprising:
- the apparatus according to claim 1;
- the instrument comprising at least one pressure sensor configured for providing the first, second and third pressure measurement signals ($p_1, p_2, p_3$) at the first, second and third measurement locations ($l_1, l_2, l_3$) within the vessel.

5. The system according to claim 4, wherein:
- the at least one pressure sensor provides the first pressure measurement signal ($p_1$) at the first measurement location ($l_1$),
- the instrument comprises a second and a third pressure sensor for providing the second and third pressure measurement signals ($p_2, p_3$) at the second and third measurement locations ($l_2, l_3$), respectively.

6. The system according to claim 4, wherein:
- the instrument is configured to provide the first, second and third pressure measurement signals ($p_1, p_2, p_3$) by subsequent changes of a position of the at least one pressure sensor along the vessel.

7. The system according to claim 4, wherein the processor is further configured to:
- receive morphological information of the vessel from an imaging unit;
- render a composite representation comprising:
  - a morphological representation of the vessel based on the morphological information; and
  - the representation of the vessel based on the first and second cross sectional areas ($A_1, A_2$) and the first and second reference positions ($r_1, r_2$).

8. The system according to claim 7, comprising the imaging unit, wherein the processor is further configured to:
- ascertain the first, second and third measurement locations ($l_1, l_2, l_3$) based on detection of at least a marker component of the instrument by the imaging unit;
- register the first, second and third measurement locations ($l_1, l_2, l_3$) with the morphological representation of the vessel.

9. A method of characterizing a vessel of a living being, comprising:
- receiving from an instrument within the vessel a first temporal pressure measurement signal ($p_1$) at a first measurement location ($l_1$), a second temporal pressure measurement signal ($p_2$) at a second measurement location ($l_2$), and a third temporal pressure measurement signal ($p_3$) at a third measurement location ($l_3$) of a pulsatile blood flow within the vessel;
- deriving a first cross sectional area ($A_1$) for a first reference position ($r_1$) of the vessel based on the first and second pressure measurement signals ($p_1, p_2$);
- deriving a second cross sectional area ($A_2$) for a second reference position ($r_2$) of the vessel based on the third pressure measurement signal ($p_3$) and one of the first and second pressure measurement signals ($p_1, p_2$), the first and second cross sectional areas ($A_1, A_2$) derived for subsequent phases (I-VI) of the pulsatile blood flow;
- rendering a representation of the vessel based on the first and second cross sectional areas ($A_1, A_2$) and the first and second reference positions ($r_1, r_2$), the representation of the vessel comprising a sequence of representations of the vessel corresponding to the subsequent phases (I-VI) of the pulsatile blood flow.

10. The method of claim 9, further comprising:
- receiving morphological information of the vessel from an imaging unit;
- composing the representation of the vessel based on the first and second cross sectional areas ($A_1, A_2$), the first and second reference positions ($r_1, r_2$) with a morphological representation of the vessel based on the morphological information.

* * * * *